United States Patent [19]

Cummins

[11] 4,340,083
[45] Jul. 20, 1982

[54] DEFLECTABLE BEAM VALVE

[75] Inventor: Richard D. Cummins, Orchard Park, N.Y.

[73] Assignee: Carleton Controls Corporation, East Aurora, N.Y.

[21] Appl. No.: 120,054

[22] Filed: Feb. 11, 1980

Related U.S. Application Data

[63] Continuation-in-part of Ser. No. 964,948, Nov. 30, 1978, abandoned.

[51] Int. Cl.³ .................... F16K 31/04; F16K 17/30
[52] U.S. Cl. ................................. 137/499; 137/504; 251/11; 251/129; 128/213 R
[58] Field of Search ............... 251/129, 11; 128/213; 137/509, 510, 504, 499

[56] References Cited

U.S. PATENT DOCUMENTS

| | | | |
|---|---|---|---|
| 3,029,743 | 4/1962 | Johns | 251/129 X |
| 3,229,956 | 1/1966 | White | 251/11 |
| 3,275,285 | 9/1966 | Morris | 251/11 |
| 3,465,732 | 9/1969 | Kattchee | 251/11 X |
| 4,053,136 | 10/1977 | Perl | 251/11 |
| 4,077,405 | 3/1978 | Haerten et al. | 128/213 X |

FOREIGN PATENT DOCUMENTS

| | | | |
|---|---|---|---|
| 608011 | 5/1978 | U.S.S.R. | 251/129 |
| 657414 | 4/1979 | U.S.S.R. | 137/499 |

Primary Examiner—Arnold Rosenthal
Attorney, Agent, or Firm—Sommer & Sommer

[57] ABSTRACT

A valve includes a piezoelectric bar mounted as a cantilevered beam. The free end of the bar is mounted for movement toward and away from a valve seat surrounding a control opening. The beam is initially flexed when in the closed position so as to maintain a fluid-tight seal with the seat. Application of an electrical signal causes the bar to flex further, thereby causing the deflectable beam portion to move away from the valve seat and permitting fluid to flow through the control opening. The beam valve may be designed to provide a substantially constant flow independent of changes in the pressure differential thereacross, and to exert a minimum closing force against a seat to provide a substantially fluidtight seal therewith in the absence of a command signal applied to the bar.

9 Claims, 6 Drawing Figures

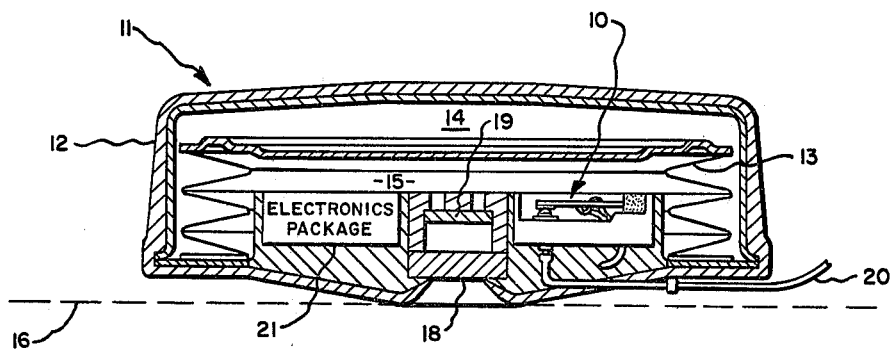
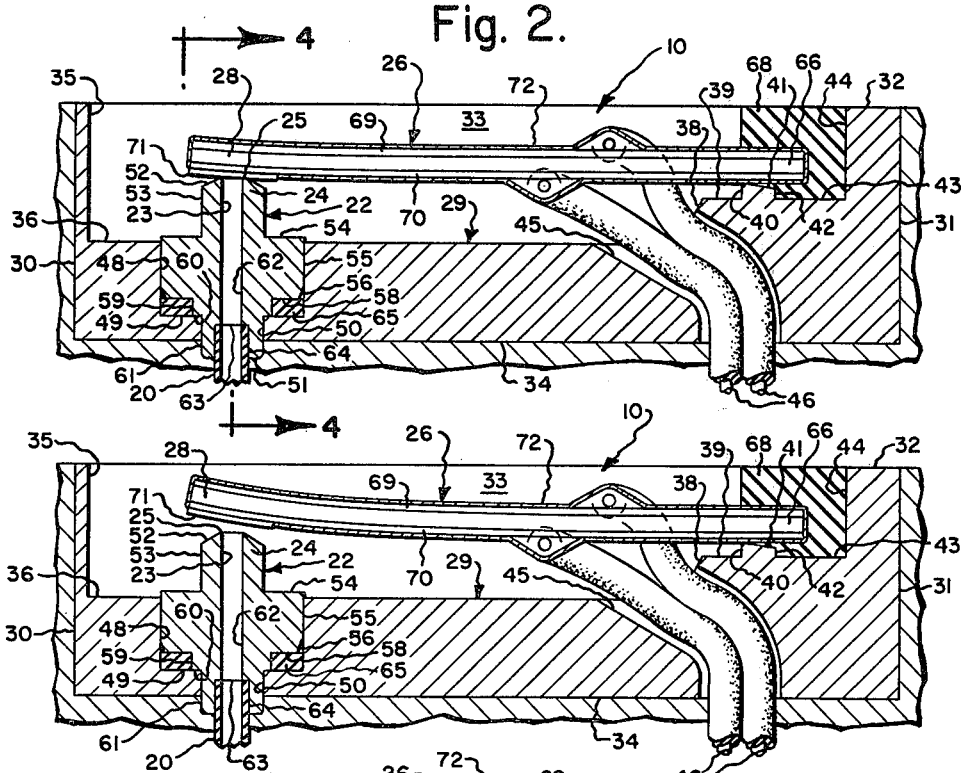
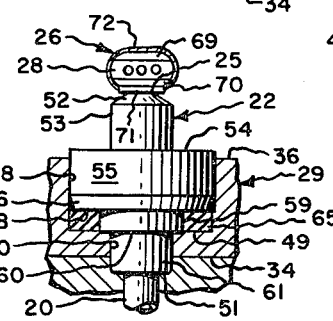

DEFLECTABLE BEAM VALVE

CROSS-REFERENCE TO RELATED APPLICATION

This application is a continuation-in-part of my pending prior application Ser. No. 964,948, filed Nov. 30, 1978, now abandoned.

BACKGROUND OF THE INVENTION

1. Field of the Invention

The present invention relates generally to the field of valves for controlling the flow of fluid through a control opening, and more particularly to an improved valve having a cantilevered piezoelectric bar, the free end of which is arranged to be selectively moved toward and away from a control opening.

2. Description of the Prior Art

Many types of valves are, of course, known. These valves generally contemplate that a member move toward and away from a valve seat.

A piezoelectric member is, in effect, an electromechanical transducer, in which application of an electrical signal produces a change in a corresponding mechanical parameter, and vice versa. Piezoelectric elements have found usage in a number of different applications, such as oscillators, switches, relays and pressure regulators. Examples of such uses are shown in U.S. Pat. Nos. 2,928,409; 3,683,212; 4,093,883; and 2,166,763.

Heretofore, diabetics would receive a large initial dose of insulin, via injection or oral medication, at one time. Recently, however, it has been proposed to implant a device in the body which would supply smaller doses of such medication at regular intervals. Examples of such implantable devices are described in U.S. Pat. No. 4,077,405, and in an article, Blackshear, Rohde, Varco and Buchwald, *One Year of Continuous Heparinization in the Dog Using a Totally Implantable Infusion Pump*, Surgery, Gynecology & Obstetrics, August, 1975, Vol. 141, pp. 176-186.

SUMMARY OF THE INVENTION

The present invention provides an improved valve, which broadly includes: a member having a passageway therethrough and having a marginal portion arranged to provide a valve seat about one end of the passageway; a piezoelectric beam having a deflectable portion mounted for movement toward and away from the seat, this member being in an initially flexed condition so that the deflectable portion will normally contact the seat and close the passageway when no electrical signal is applied to the beam; and control means operatively arranged to supply an electrical signal to the beam for selectively controlling movement of the deflectable portion relative to the seat. The position of the deflectable portion relative to the seat controls the flow of fluid through the passageway.

The improved valve may be designed to provide a substantially constant flow independent of changes in the pressure differential thereacross and/or to exert a minimum closing force against a seat so as to provide a substantially fluid-tight seal therewith in the absence of a command signal applied to the beam.

In the preferred embodiment, the beam is mounted as a cantilever and is flexed further in the same direction as the deflectable portion moves away from the seat.

Accordingly, a general object of the present invention is to provide an improved valve.

Another object is to provide an improved valve which will fail in a closed position in the event of a malfunction.

Another object is to provide an improved valve which is capable of permitting a substantially constant flow therethrough independent of changes in the differential pressure thereacross.

Another object is to provide an improved valve in which a movable portion is biased to engage a seat with a preload force to establish a fluid-tight seal in the absence of an electrical command to the valve.

Another object is to provide an improved valve which is relatively small and compact, and which has a minimum number of moving parts.

Another object is to provide an improved valve which is particularly adapted for use in a device which may be implanted into the body of a human or an animal to provide a metered flow of a medication, such as insulin or the like, either continuously or at regular intervals.

These and other objects and advantages will become apparent from the foregoing and ongoing written specification, the drawings, and the appended claims.

BRIEF DESCRIPTION OF THE DRAWINGS

FIG. 1 is a fragmentary sectional view of an implantable device incorporating the improved valve.

FIG. 2 is an enlarged view of the valve shown in FIG. 1, this view depicting the beam in its "closed" position.

FIG. 3 is a view similar to the view of FIG. 2, but showing the beam as having been further flexed so that the valve is in its "open" position.

FIG. 4 is a fragmentary transverse vertical sectional view thereof, taken generally on line 4—4 of FIG. 2, showing the beam and seat member in end elevation.

DESCRIPTION OF THE PREFERRED EMBODIMENTS

Figure 5:
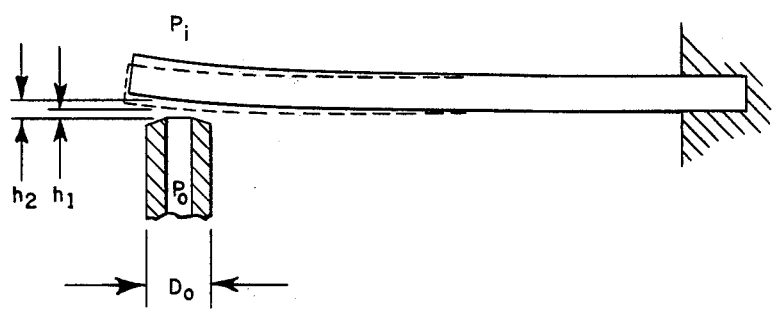
FIG. 5 is a schematic view of the valve and seat, illustrating the preferred operation of the valve to permit a substantially constant flow within a working range of differential pressures.

At the outset, it should be clearly understood that like reference numerals are intended to identify the same elements and/or structure consistently throughout the several drawing figures, as such elements and/or structure may be further described or explained by the entire written specification of which this detailed description is an integral part.

Referring now to the drawings, and more particularly to FIG. 1 thereof, the invention provides an improved valve, of which the presently preferred embodiment is generally indicated at 10.

The Improved Structure

In FIG. 1, valve 10 is shown as being incorporated into a larger device 11 which may be implanted into the body of a human or an animal, and used to control the flow of a suitable medication, such as insulin or the like. Briefly, the device 11 is shown as having a casing 12 containing therewithin a bellows-type device or reservoir 13 which separates a pressurizing chamber 14 from a medication chamber 15. The device 11 is adapted to be implanted in a body beneath the skin line 16 so that an inlet septum 18 will be externally exposed. A needle stop 19 is arranged behind the inlet septum to limit the travel of an injected needle or syringe (not shown) by which the medication chamber 15 may be refilled. Valve 10 is exposed to the medication in chamber 15, and is used to control the flow of such medication exiting the device via outlet flow tube 20. The operation of valve 10 is controlled by an electronics package 21, which contains a battery power source (not shown) and suitable circuitry (not shown). A pressure differential is maintained between chambers 14 and 15 so that valve 10 may be selectively operated to control the flow of medication leaving chamber 15.

The purpose of illustrating implantable device 11 is merely to show one particular environment in which the improved valve may be used. However, it should be clearly understood that valve 10 possesses general utility apart from this specific environment, and may be widely used in other applications to control the flow of a fluid (i.e., a liquid or gas) through a passageway or control opening.

Referring now to FIG. 2, the improved valve 10 is broadly shown as including a member, generally indicated at 22, having a passageway 23 therethrough and having a marginal portion 24 arranged to provide an annular valve seat 25 about the upper end of the passageway; a piezoelectric beam, generally indicated at 26, having a deflectable portion 28 mounted for movement toward and away from seat 25; and control means, such as electronics package 21, operatively arranged to supply a suitable electrical signal to beam 26 for selectively controlling the movement of the beam's deflectable portion 28 relative to valve seat 25.

Member 22 and beam 26 are both mounted in a recessed cavity of a block, generally indicated at 29, which in turn is suitably mounted on the device 11. In FIG. 2, this supportive block 29 is shown as having a planar vertical left end face 30; a planar vertical right end face 31; a planar horizontal upper surface 32, from which a recess 33 extends downwardly into the block; and a planar horizontal lower surface 34. Recess 33 is bounded by, from left to right in FIG. 2, a rightwardly-facing vertical left surface 35 extending downwardly from upper surface 32, a horizontal surface 36, an upwardly and rightwardly inclined surface 38, a horizontal surface 39, a leftwardly-facing vertical surface 40, a downwardly and rightwardly inclined surface 41, a rightwardly-facing vertical surface 42, a horizontal surface 43, and a leftwardly-facing vertical surface 44 extending upwardly therefrom to join block upper surface 32. Two openings are provided through the block so as to communicate its lower surface 34 with the recess. A first opening 45 is provided to accommodate passage of a pair of insulated conductors, severally indicated at 46, connecting beam 26 with electronics package 21. The second opening is arranged to receive seat member 22, and is bounded by an upper cylindrical surface 48 extending downwardly from recess surface 36, an upwardly-facing annular horizontal shoulder 49, and a lower cylindrical surface 50 continuing downwardly to join block lower surface 34.

The seat member 22 is shown as having an upper annular seating edge 25; a lower annular horizontal surface 51; an outer surface including, from top to bottom in FIG. 2, a downwardly-divergent frusto-conical surface 52 extending away from seat 25, a cylindrical surface 53 continuing downwardly therefrom, an upwardly-facing annular horizontal surface 54, a cylindrical surface 55, a downwardly-convergent surface 56, a downwardly-facing annular horizontal surface 58, a cylindrical surface 59, a downwardly-facing annular horizontal surface 60, and a cylindrical surface 61 continuing downwardly therefrom to join seat member lower surface 51; and a central vertical throughbore or passageway bounded by an upper cylindrical surface 62 extending downwardly from seating edge 25, a downwardly-facing annular horizontal surface 63, and a lower cylindrical surface 64 continuing downwardly therefrom to join seat member lower surface 51. An O-Ring or resilient washer 65 is compressed between the seat member and the supportive block to provide a fluid-tight seal therebetween. The seat member 22 may be press-fitted into the receptive opening, as shown, or a mating threaded connection may be alternatively provided therebetween.

In the preferred embodiment, beam 26 is a horizontally-elongated piezoelectric bar having its rightward marginal end portion 66 embedded in a dielectric block 68, suitably secured to the supportive block 29. Hence, beam 26 is mounted as a cantilever with its rightward marginal end fixed, and with its leftward deflectable marginal end 28 arranged to move toward and away from valve seat 25. Insulated conductors 46, 46 from the electronics package, are shown as penetrating opening 45 and being connected to the beam's upper and lower metallic strips 69, 70, respectively. The underside of the beam's deflectable end 28 is shown as carrying a resilient gasket 71, typically a silicone rubber, which insures a fluid-tight seal with valve seat 25 when the valve is in its closed position (FIG. 2). Moreover, the entire beam 26 may be covered with a suitable dielectric coating 72 which will insulate the beam's upper and lower metallic strips, and protect the beam from possible chemical attack by the medication.

The position of the piezoelectric beam, when the valve is in its closed position, is shown in FIG. 2. It should be noted that, in this position, the free end of the beam is in an upwardly deflected position so as to initially flex the beam and to insure a fluid-tight sealed engagement between gasket 71 and seat 25. It should also be noted that the beam will assume this initially flexed condition in the absence of any electrical signal supplied by the electronics package 21. Hence, this initial flex of the beam insures that, in the event of an electrical non-function, the valve will assume a "fail-closed" position.

It is known that application of a suitable voltage to a cantilevered piezoelectric bar will cause the bar to "curl", much in the same manner as a bimetallic strip responds to differences in temperature. Deflection of the beam's free end 28 away from the seat 25 uncovers the passageway, as shown in FIG. 3, and permits medication from chamber 15 to flow through the passageway and the outlet flow tube 20. The amplitude of such deflection of the beam's free end is a function of the magnitude and polarity of the applied voltage. Hence, the amount of flow may be controlled by varying the amplitude of such beam deflection, or the duration of such deflection, or both. While the beam's deflection is somewhat exaggerated in FIG. 3 for purposes of illustration, the magnitude of such deflection from the closed to the open position may be on the order of 0.001 inch.

The electronics package 21 may take many forms to selectively deflect the beam and obtain the desired flow rate. For example, the electronics package might comprise a simple switch arranged to supply a voltage, of desired magnitude and polarity, from the battery power source to the beam, either at regular time intervals or in response to a sensed need for medication. The electronics package might include a means for sensing the amount of glucose in a body fluid, and cause the valve to open whenever such sensed valve falls below a predetermined minimum. Reversal of the polarity of such applied voltage will cause the valve to snap closed. Hence, the electronics package could be easily designed to reverse the polarity of the applied voltage at the end of a time interval so as to afford an "open-closed" mode of operation. Alternatively, the applied voltage could be caused to decay over a period of time so as to afford a "snap open-slowly close" mode of operation. Therefore, the electronics package 21 contemplates many different circuits for operatively connecting the power source with the beam so as to provide the desired operational characteristics. Inasmuch as these characteristics may vary, the specific circuitry is considered to be a matter of design choice, well within the ambit of a person skilled in this art.

Substantially Constant Flow Rate

The improved valve may also be consciously designed to permit a substantially constant flow rate through the valve over a working range of differential pressures thereacross. As used herein, a substantially constant flow rate is defined to be one in which the rate of flow does not vary by more than twenty percent from a desired value. This twenty percent margin of deviance is generally believed to afford a working range of considerable width. The margin of deviance is generally directly related to the width of the working range; that is, the smaller the margin for deviance, the narrower the width of the working range.

In FIG. 5, the beam is illustrated in two positions: the dashed line indicating the initial position of the deflectable end portion when an electrical signal has commanded the valve to open and the pressure differential across the valve is relatively high; and the solid line indicating a new position of the deflectable portion displaced further away from the seat, this change in position being caused by a decrease in such pressure differential as fluid is supplied from the pressurized bellows-type reservoir. In FIG. 5, $p_i$, represents the pressure within medication chamber 15, and $p_o$ indicates the pressure in outlet passageway 23. Hence, the pressure differential across the valve, $\Delta p$, indicates the differences between $p_i$ and $p_o$. In normal use, $p_i$ is greater than $p_o$ so that medication will flow from the reservoir to the body when the valve is opened.

The reference characters $h_1$ and $h_2$ indicate the displacement of the deflectable end portion from the seat in the solid and phantom positions shown, respectively. In other words, as the pressure differential falls, the deflectable end portion will move from position $h_1$ further away from the seat to position $h_2$.

In this condition, the beam may be regarded as having a spring rate, K, which causes a change in displacement ($h=h_2-h_1$) because of a change in force. Or, $$\text{Spring rate of beam } (K) = \frac{\text{Force}}{\text{Displacement } (\Delta h = h_2 - h_1)} \quad [1]$$

However, after the beam has been opened, the pressure differential acts on the projected seating area, $A_s$, to exert a net downward force, $F_f$, which urges the deflectable portion to move closer to the seat. Or, $$F_f = \Delta p A_{seat} = \frac{\Delta p \pi D_o^2}{4} \quad [2]$$

Where $D_o$ is the outside diameter of the seat.

Hence, an electrical command signal supplied to the bar causes the bar to curl, thereby moving the deflectable end portion away from the seat. If no pressure differential existed across the valve, the deflectable end portion would theoretically move to the commanded position. However, in actual practice, a pressure differential across the valve exerts a net force $F_f$ which urges the valve to close. The magnitude of this closing force, $F_f$, decreases as the pressure differential falls, as by medication being dispensed from the reservoir to the body. The effect of this decreasing force is to allow the deflectable end portion to move further away from the seat, thereby permitting an increased opening through which fluid may flow. In other words, the valve compensates for a decrease in the driving force, $\Delta p$, by providing an enlarged opening through which fluid may flow.

Flow through the valve may be calculated by the formula:

$$\text{Flow} = c(\Delta p)^{\frac{1}{2}} (h - \Delta h) \quad [3]$$

where
c = constant
$\Delta p$ = pressure differential across valve = $p_i - p_o$
h = commanded position of beam (i.e., distance from seat to which beam would move if there were no pressure differential across valve.)
$\Delta h$ = amount of beam displacement toward seat due to effect of pressure differential across valve.

Equations [1] and [2] can be solved for $\Delta h$ as follows:

$$\Delta h = \frac{F}{K} = \frac{\Delta p A_s}{K} \quad [4]$$

Substituting this into equation [3]:

$$\text{Flow} = c(\Delta p)^{\frac{1}{2}} \left[ h - \frac{(\Delta p)A}{K} \right] \quad [5]$$

Or, $$\text{Flow} = ch(\Delta p)^{\frac{1}{2}} - \frac{cA}{K} (\Delta p)^{3/2} \quad [6]$$

Figure 6:
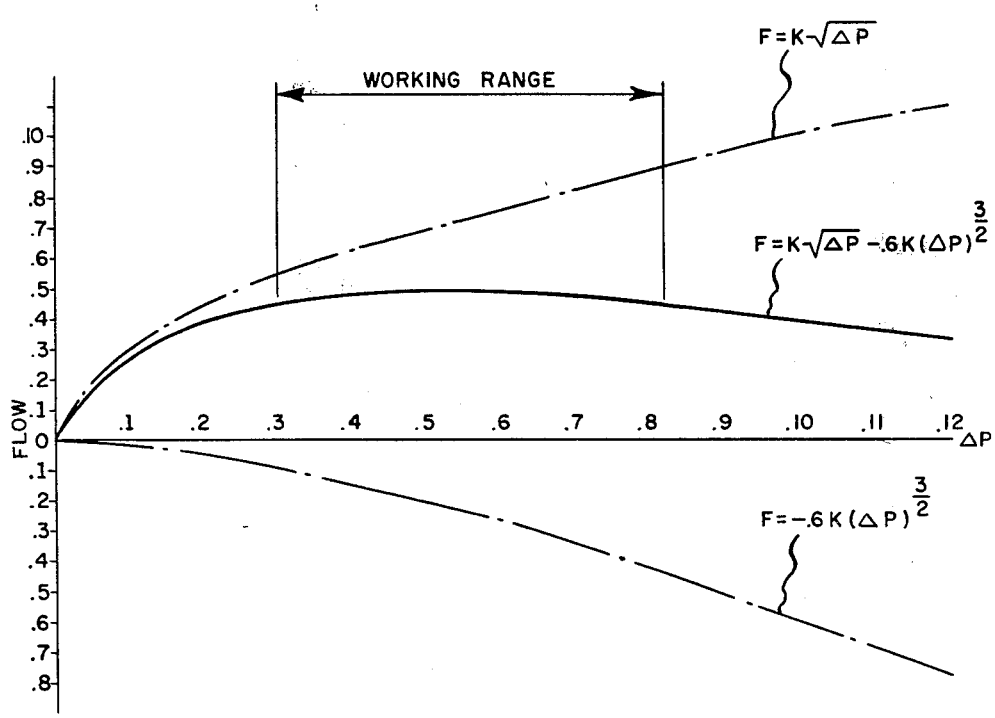
FIG. 6 is a graph of flow versus differential pressure, and illustrating the manner in which the valve may be designed to permit a substantially constant flow over a working range of differential pressures.

The significance of equation [6] is graphically illustrated in FIG. 6, in which the solid curve has been obtained by superimposing the two dashed curves. For the purpose of illustration, the value of ch was selected to be unity, and the value of (cA)/K was selected to be 0.6. However, persons skilled in this art will readily appreciate that the beam and seat may be consciously designed to have different values of c, h, A and K, thereby to alter the shapes of the curves.

In the illustrative curve depicted in FIG. 6, it can be seen that the solid curve has an intermediate relatively "flat" portion, denominated the "working range", within which changes in Δp do not produce substantial changes in flow. By varying the values of the constants, c, h, A and K, the location and width of the "flat" portion can be tailored to provide a substantially constant flow over a desired "working range".

From equation [6], it will be noted that flow will be zero when Δp is zero. However, flow will also be zero, when:

$$\text{Flow} = o = ch(\Delta p)^{\frac{1}{2}} - \frac{cA(\Delta p)^{3/2}}{K} \quad [7]$$

Or, $$h(\Delta p)^{\frac{1}{2}} = \frac{A}{K} (\Delta p)^{3/2} \quad [8]$$

Or, $$\Delta p = \frac{Kh}{A}$$

Hence, by selecting appropriate constants, the valve may be designed so as to provide substantially constant flow within a "working range" of differential pressures.

Minimum Preload Force

As previously noted, it is presently preferred that the beam be in an initially flexed condition when it engages the seat so that such preload force will insure a fluid-tight sealed engagement between gasket 71 and seat 25.

When a pressure differential exists across the valve, the magnitude of the closing force is the sum of the amount of such preload, and a supplemental force caused by the differential pressure acting over the seat area:

$$F_{closing} = \text{cantilever preload} + \Delta p A_s \quad [10]$$

This closing force exerts a squeezing pressure on the seat as follows:

$$P_{squeeze} = \frac{F_{closing}}{\text{seat area}} = \frac{F_{closing}}{\frac{\pi(D_o - D_i)2}{4}} \quad [11]$$

To insure that a fluid-tight connection is made between the deflectable portion and the seat, the seat squeeze pressure must be greater than the pressure differential across the valve. Or, $$P_{squeeze} > \Delta p = P_i - P_o \quad [12]$$

Therefore, the improved valve is generally adapted to control the flow of a fluid, and is particularly suited for use in an implantable device of the type shown. The invention contemplates that various additional changes and modifications may be made. For example, the beam need not necessarily be mounted as a cantilever. Alternatively, it may be fixed at both ends such that an intermediate portion will be deflectable. Of course, this is not exhaustive of the many ways in which the beam may be mounted, as persons skilled in this art will readily appreciate. The particular type and shape of the piezoelectric element is also considered to be a matter of design choice.

Therefore, while the presently preferred embodiment of the improved valve has been illustrated and described, persons skilled in this art will recognize that various changes and modifications may be made without departing from the spirit of the invention, as defined by the following claims.

What is claimed is:

1. A valve, comprising:
   a member having a passageway therethrough and having a marginal end portion arranged to provide a valve seat about one end of said passageway;
   a piezoelectric beam arranged on the upstream side of said member and having a deflectable portion mounted for movement toward and away from said seat, said deflectable portion being selectively movable away from said seat toward an initially commanded position, the magnitude of the pressure differential across said member exerting a closing force which urges said deflectable portion to move away from said commanded position toward said seat, said beam having a spring rate such that said deflectable portion will move further away from said seat as said pressure differential decreases to permit a substantially constant flow of fluid through said passageway over a working range of differential pressure across said valve when said deflectable portion has been moved away from said seat; and
   control means operatively arranged to supply an electrical signal to said beam for selectively causing said deflectable portion to move away from said seat;
   whereby the position of said deflectable portion relative to said seat may control a flow of fluid through said passageway.

2. A valve as set forth in claim 1 wherein the rate of said flow does not vary by more than twenty percent within said working range.

3. A valve as set forth in claim 1 wherein said beam is mounted as a cantilever.

4. A valve as set forth in claim 1 wherein said beam is in an initially flexed condition such that said deflectable portion will normally contact and be pressed against said seat to close said passageway in the absence of an electrical signal supplied to said beam.

5. In a fluid-dispensing device adapted to be implanted within the body of a mammal, said device having a pressurized reservoir containing a fluid to be selectively dispensed to said body, the improvement which comprises: an improved valve mounted on said device and operatively arranged to meter the flow of fluid from said reservoir to said body, said valve including
   a member having a passageway therethrough and having a marginal end portion arranged to provide a valve seat about one end of said passageway, said passageway communicating said reservoir with said body;
   a piezoelectric beam arranged in said reservoir and having a deflectable portion mounted for movement toward and away from said seat, said deflectable portion being selectively movable away from said seat toward an initially commanded position, the magnitude of the pressure differential across said member exerting a closing force which urges said deflectable portion to move away from said commanded position toward said seat, said beam having a spring rate such that said deflectable portion will move further away from said seat as said pressure differential decreases to permit a substantially constant flow of fluid through said passageway over a working range of differential pressure across said valve when said deflectable portion has been moved away from said seat, said beam being in an initially flexed condition so that said deflectable portion will normally contact said seat and close said passageway in the absence of an electrical signal supplied to said beam; and control means operatively arranged to supply an electrical signal to said beam for selectively causing said deflectable portion to move away from said seat;

whereby the position of said deflectable portion relative to said seat may control a flow of fluid through said passageway.

6. The improvement as set forth in claim 5 wherein said beam is mounted as a cantilever.

7. The improvement as set forth in claim 5 wherein said beam is flexed further in the same direction as said deflectable portion moves away from said seat.

8. The improvement as set forth in claim 5 wherein said beam is coated with a dielectric material.

9. The improvement as set forth in claim 5 wherein the rate of said flow does not vary by more than twenty percent within said working range.

* * * * *